(12) United States Patent
Kaul et al.

(10) Patent No.: US 12,399,177 B2
(45) Date of Patent: *Aug. 26, 2025

(54) COMBINATION TREPONEMAL AND NON-TREPONEMAL SYPHILIS TEST

(71) Applicant: Bio-Rad Laboratories, Inc., Hercules, CA (US)

(72) Inventors: Ravi Kaul, Davis, CA (US); Weiming Zheng, Emeryville, CA (US); Roger Walker, Benicia, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/437,816

(22) Filed: Feb. 9, 2024

(65) Prior Publication Data

US 2024/0248086 A1 Jul. 25, 2024

Related U.S. Application Data

(60) Division of application No. 17/170,577, filed on Feb. 8, 2021, now Pat. No. 11,913,954, which is a continuation of application No. 16/832,608, filed on Mar. 27, 2020, now Pat. No. 10,942,182, which is a division of application No. 16/405,588, filed on May 7, 2019, now Pat. No. 10,648,981, which is a continuation of application No. 15/701,272, filed on Sep. 11, 2017, now Pat. No. 10,324,091, which is a continuation of application No. PCT/US2016/021379, filed on Mar. 8, 2016.

(60) Provisional application No. 62/181,685, filed on Jun. 18, 2015, provisional application No. 62/131,062, filed on Mar. 10, 2015.

(51) Int. Cl.
| | |
|---|---|
| *G01N 33/571* | (2006.01) |
| *G01N 33/543* | (2006.01) |
| *G01N 33/92* | (2006.01) |

(52) U.S. Cl.
CPC ......... *G01N 33/571* (2013.01); *G01N 33/543* (2013.01); *G01N 33/54313* (2013.01); *G01N 33/92* (2013.01); *G01N 2333/20* (2013.01); *G01N 2405/04* (2013.01); *G01N 2469/20* (2013.01)

(58) Field of Classification Search
CPC .................................................... G01N 33/571
See application file for complete search history.

(56) References Cited

U.S. PATENT DOCUMENTS

| | | | | |
|---|---|---|---|---|
| 2003/0124564 A1* | 7/2003 | Trau | ...................... | C08G 77/06 435/6.12 |
| 2013/0345081 A1* | 12/2013 | King | ................... | C12N 9/1044 506/18 |
| 2014/0322800 A1* | 10/2014 | Castro | .................. | G01N 33/564 435/287.2 |

* cited by examiner

*Primary Examiner* — Albert M Navarro
(74) *Attorney, Agent, or Firm* — Kilpatrick Townsend & Stockton LLP

(57) ABSTRACT

Provided herein are multiplex assays for detecting antibodies indicative of presence and stage of syphilis infection in an individual. Individuals infected with syphilis produce antibodies directed to syphilis components and the lipid cellular debris associated with the infection. The present disclosure represents the first combination of these diverse antibody targets in a single assay.

14 Claims, 2 Drawing Sheets

COMBINATION TREPONEMAL AND NON-TREPONEMAL SYPHILIS TEST

CROSS-REFERENCE TO RELATED APPLICATIONS

This application is a divisional application of U.S. patent application Ser. No. 17/170,577, filed Feb. 8, 2021; which is a continuation application of U.S. patent application Ser. No. 16/832,608, filed Mar. 27, 2020, issued Mar. 9, 2021 as U.S. Pat. No. 10,942,182; which is a divisional application of U.S. application Ser. No. 16/405,588, filed May 7, 2019, issued May 12, 2020 as U.S. Pat. No. 10,648,981; which is a continuation application of U.S. patent application Ser. No. 15/701,272, filed Sep. 11, 2017, issued Jun. 18, 2019 as U.S. Pat. No. 10,324,091; which is a continuation application of International Application No. PCT/US2016/021379, filed Mar. 8, 2016; which claims benefit of priority to U.S. Provisional Patent Application No. 62/131,062, filed Mar. 10, 2015 and U.S. Provisional Patent Application No. 62/181,685, filed Jun. 18, 2015. Each application is incorporated by reference in its entirety.

BACKGROUND OF THE INVENTION

Syphilis is a sexually transmitted disease (STD) caused by the spirochete bacterium *Treponema pallidum*. Serological tests for syphilis can be classified into two groups, non-treponemal and treponemal tests. Nontreponemal tests detect nontreponemal antibodies (reagin) against lipoidal material released from damaged host cells. The most widely used nontreponemal tests are Venereal Diseases Research Laboratory (VDRL) and rapid plasma reagin (RPR) tests, which are tests (usually flocculation tests) employing a cardiolipin-lecithin-cholesterol-based antigen. Nontreponemal tests have the advantage of being widely available, inexpensive and convenient to perform. Results for these tests usually revert to negative after successful treatment, so they can be used to monitor response to therapy. These tests typically require subjective interpretation however, so they are difficult to interpret, particularly for weakly reactive sera. The nontreponemal tests also have limited potential for high-volume testing and automation. In contrast, the treponemal tests detect antibodies directed against native or recombinant surface antigens of *T. pallidum* such as 15 kDa, 17 kDa, and 47 kDa proteins. Treponemal tests include *T. pallidum* passive particle agglutination (TP-PA) assay, the fluorescent treponemal antibody absorption (FTA-ABS) test, and most enzyme immunoassays (EIA) tests. Compared to nontreponemal tests, treponemal tests exhibit higher specificity and sensitivity. They cannot, however, be used to monitor response to therapy because treponemal antibodies remain for years after infection.

Syphilis is diagnosed using either traditional algorithm (patient specimen screened by nontreponemal test followed by tremonemal test confirmation) or reverse algorithm (patient specimen screened by treponemal test followed by nontreponemal confirmation). Essentially, both algorithms follow a positive initial screen with a confirmation test.

BRIEF SUMMARY OF THE INVENTION

Provided herein are kits to detect nontreponemal and treponemal antibodies in a sample from an individual suspected of having a syphilis infection. In some embodiments, the kit includes (i) a solid support (e.g., microparticles, beads, or surface such as a chip, microtiter plate, membrane, or glass) coated with a lipoidal antigen (e.g., cardiolipin, lecithin, cholesterol, or a mixture thereof); and (ii) a solid support (e.g., microparticles, beads, or surface such as a chip, microtiter plate, membrane, or glass) coated with *Treponema pallidum* antigen. In some embodiments, (i) and (ii) are packaged in the same compartment (e.g., in the same mixture in a vessel or tube, or coated on the same surface, e.g., of an ELISA well). In some embodiments, (i) and (ii) are packaged in separate compartments. In some embodiments, the beads are in storage buffer comprising pH buffer (e.g., Trizma, glycine, phosphate) and salt (e.g., NaCl). In some embodiments, the storage buffer further includes an ionic or zwitterionic detergent. In some embodiments, the kit further comprises an assay buffer and/or sample dilution buffer. In some embodiments, the storage buffer, the assay buffer, and/or sample dilution buffer lacks non-ionic detergent.

In some embodiments, the lipoidal antigen is cardiolipin, lecithin or cholesterol. In some embodiments, the *Treponema pallidum* antigen is r15, r17, r47, a mixture thereof, or a fusion of r17 and r47.

In some embodiments, the kit further includes a labeled anti-immunoglobulin (Ig) antibody, e.g., an anti-human Ig antibody. In some embodiments, the anti-Ig antibody is specific for IgG (e.g., human IgG) and/or IgM (e.g., anti-human IgM). In some embodiments, the labeled, anti-human immunoglobulin antibody is an antibody conjugate that binds human IgG and human IgM. In some embodiments, the kit comprises a first labeled, anti-human Ig antibody specific for IgG and a second labeled, anti-human Ig antibody specific for IgM. The anti-human IgG antibody and anti-human IgM antibody can have the same or different labels.

In some embodiments, the kit further includes a wash solution or wash stock solution (e.g., concentrate or dehydrated). In some embodiments, the wash solution or wash stock solution includes PBS, and optionally an ionic, non-ionic, or zwitterionic detergent. In some embodiments, the wash solution has non-ionic detergent. In some embodiments, the wash solution lacks non-ionic detergent.

In some embodiments, the lipoidal antigen is coupled (attached) to the solid support of (i) via an ionic interaction. In some embodiments, the solid support of (i) is coated with polyethylenimine (PEI). In some embodiments the *Treponema pallidum* antigen is coupled to the solid support of (ii) via a covalent interaction. In some embodiments, the solid supports (e.g., microparticles or beads) of (i) and (ii) are differently labeled, of different sizes, or of different weights.

In some embodiments, the kit further comprises at least one control agent. In some embodiments, the control agent is an internal control agent, e.g., to be used in the same reaction tube or vessel with the assay reagents and sample. In such case, the internal control is distinguishable from other solid supports, e.g., with a distinct label or weight, as described in more detail herein. In some embodiments, the control reagent is a solid support, wherein the solid support is conjugated to an agent that binds specimen specific analyte (e.g., a specimen verification control, e.g., a serum verification bead). Thus in some embodiments, the kit further comprises (iii) beads coated with a sample quality control reagent (e.g., a serum verification bead (SVB) coated with a reagent that reacts with common serum element, such as an antibody specific for a coagulation factor (e.g., FXIII), globulin, or albumin)). In some embodiments, the kit further comprises a control comprising a solid support lacking reagent as a blank, e.g., (iv) a reagent blank bead (RBB). In some embodiments, the kit further comprises a control to determine the quality of signal, e.g., a solid support labeled with a known label or combination of labels. For example, in some embodiments, the kit includes (v) a signal quality control bead (e.g., an internal standard bead (ISB) with intrinsic fluorescence). In some embodiments, the kit only includes one of (iii), (iv), or (v). In some embodiments, the kit includes (iii), (iv), and (v). In some embodiments, the kit includes any combination of two of the controls (e.g., (iii) and (iv), (iii) and (v), or (iv) and (v)).

Further provided are methods of detecting the presence of syphilis antibodies in a sample, e.g., a biological sample from an individual, e.g., a human. In some embodiments, the method comprises (a) contacting the sample with (i) solid support (e.g., microparticles, beads, or surface) coated with lipoidal antigen (e.g., cardiolipin-lecitin-cholesterol antigen) and (ii) solid support (e.g., microparticles, beads, or surface) coated with *Treponema pallidum* antigen in the same compartment, thereby forming a sample-support (e.g., sample-bead) mixture; (b) washing the sample-support mixture to remove unbound sample; (c) contacting the sample-support mixture with a labeled, anti-immunoglobulin (Ig) antibody (e.g., anti-human Ig antibody); and (d) detecting the presence of syphilis antibodies by detecting the label on the anti-Ig antibody. In some embodiments, step (a) and/or step (c) are carried out in a buffer that does not include non-ionic detergent.

In some embodiments, the method further comprises washing to remove unbound anti-Ig antibody between steps (c) and (d). In some embodiments, the washing is carried out with non-ionic detergent. In some embodiments, the washing is carried out in the absence of non-ionic detergent. In some embodiments, the washing is carried out with phosphate buffered saline (PBS), optionally with ionic, non-ionic, or zwitterionic detergent. In some embodiments, non-ionic detergent is used in wash buffers in the presently described assays, but at a lower concentration than in standard assays having hydrophilic (non-lipid) components. In some embodiments, washing with non-ionic detergent is carried out with reduced duration compared to standard assays having hydrophilic (non-lipid) components (e.g., 2-20, 1-10, or 2-8 seconds, compared to 10-60, or 30-90 seconds). In some embodiments, fewer washes are carried out with non-ionic detergent compared to standard assay's having hydrophilic (non-lipid) components (e.g., 2-4, 2, 3, or 4 times over duration of assay, compared to 4, 8, or 5-10 times).

In some embodiments, the labeled anti-Ig antibody is anti-human Ig. In some embodiments, the labeled anti-human Ig antibody is specific for IgG and/or IgM. In some embodiments, the labeled, anti-human immunoglobulin antibody is an antibody conjugate that binds human IgG and human IgM. In some embodiments, step (c) comprises contacting the sample-support mixture with a first labeled, anti-human Ig antibody specific for IgG and a second labeled, anti-human Ig antibody specific for IgM. The first and second labeled antibodies can be labeled with the same or with different labels.

In some embodiments, the method further comprises prescribing a course of treatment if syphilis antibodies are detected in step (d). In some embodiments, course of treatment includes treatment with an antibiotic (e.g., penicillin, tetracycline, doxycycline, etc.).

DETAILED DESCRIPTION OF THE INVENTION

A. Introduction

Figure 1:
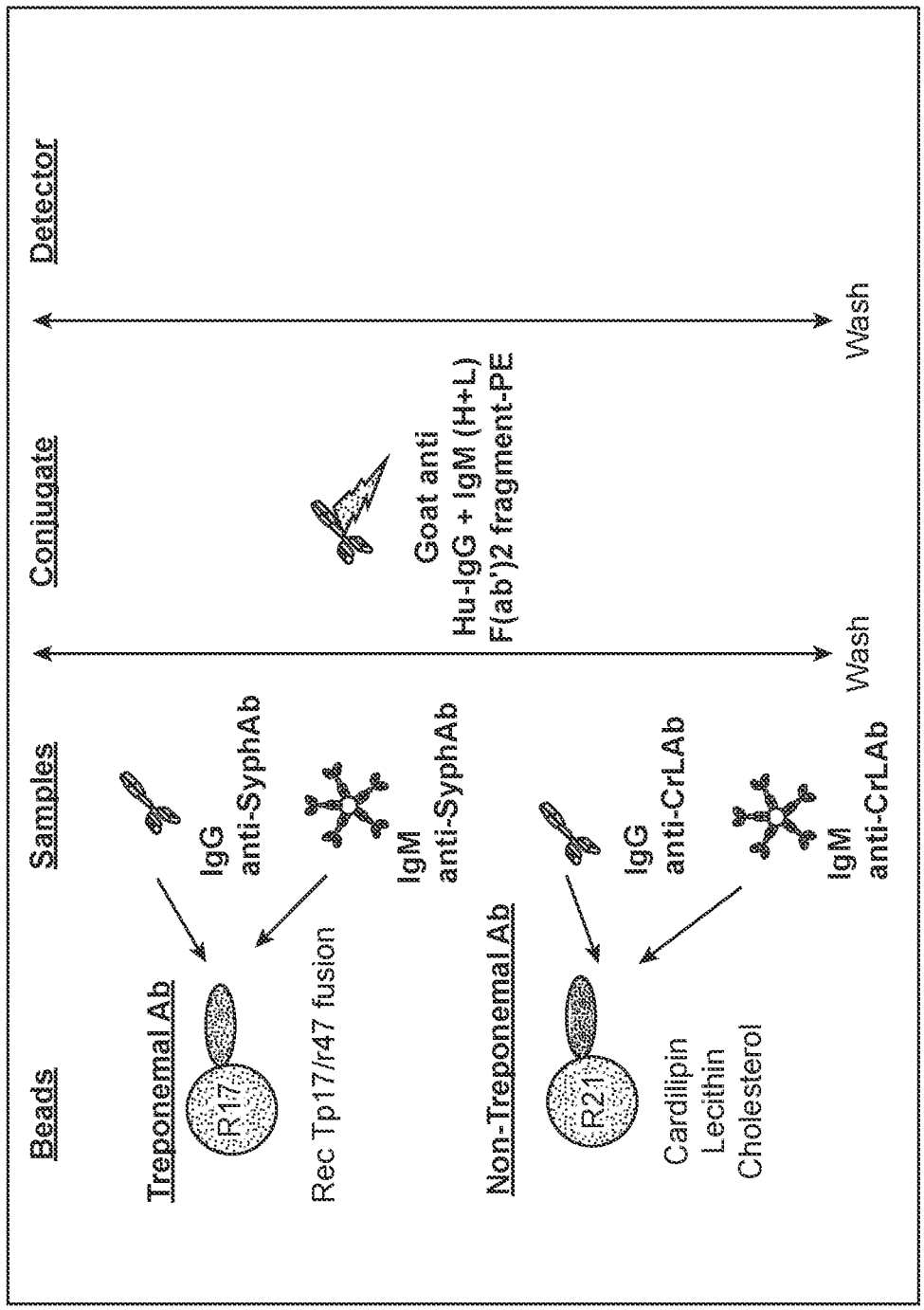
FIG. 1 shows the schematic illustration of a combo test for the detection of both treponemal and nontreponemal antibodies on an automated platform (e.g., BioPlex™ 2200).

Described herein is a novel combination test for simultaneous detection of treponemal and nontreponemal antibodies in patient samples. The assays can be performed efficiently on an automated platform. The combination test comprises a treponemal test (e.g., beads labeled with a first label and coated with *T. pallidum* recombinant r17 and r47 fusion protein), and a nontreponemal test (e.g., beads labeled with a second label and an antigen mixture of cardiolipin-lecithin-cholesterol). The combination test can also comprise labeled anti-human IgG and labeled anti-human IgM reporters (e.g., anti-hIgG-PE and anti-hIgM-PE) to quantify the treponemal and nontreponemal antibodies in the specimen.

The combination of (i) beads covalently linked to antigen (treponemal) with (ii) beads non-covalently coated with a lipid antigen (nontreponemal) in a single assay or kit is not straightforward because different conditions are generally used for storage and washing of the two types of beads. Using the presently disclosed conjugation techniques and buffer conditions, however, the combined reagents are stable for at least 12-24 months. In addition, the assays are sensitive and accurate in spite of lack of non-ionic detergent in the storage solution (in which the solid support or beads are stored), sample dilution buffer, and assay solution (in which sample is incubated with the beads). Typically, non-ionic detergents are used in various solutions to reduce background signal, but as shown herein, assays combining both amine-functionalized beads coated with hydrophobic nontreponemal antigen and beads coated with hydrophilic treponemal antigen detected antibodies with high accuracy in Syphilis patients at various stages of infection and treatment. In some embodiments, non-ionic detergent is used in wash buffers in the presently described assays, but at a lower concentration than in standard assays having hydrophilic (non-lipid) components. In some embodiments, washing with non-ionic detergent is carried out with reduced duration or frequency compared to standard assays having hydrophilic (non-lipid) components.

Combining the two types of beads with different affinities and complexity involved process modification, such as omitting detergents from the sample diluent. The two types of beads would typically be stored and used in distinct conditions: no one has combined the two formats i.e., hydrophilic and hydrophobic micro environments in one assay.

Further, the results described herein identify reagin-specific IgM and IgG antibodies using IgM-PE and IgG-PE conjugates. This approach has helped detect the presence of IgM antibodies among reagin positive patients. Indeed, we determined that the majority of anti-reagin antibodies are of the IgM isotype. Current assays report reactive/non-reactive results without identifying the isotype of the antibodies. IgM isotype antibodies are indicative of early stage acute infection, and IgG isotype antibodies become prevalent later. Loss or decrease of RPR specific IgM antibodies can allow a physician to monitor and prescribe drug treatment appropriately (e.g., prescribing a higher or more frequent dose of antibiotics for more advanced infections). In some embodiments, stage can be determined by detecting anti-IgM-PE or anti-IgG-PE alone, or by using different labels on the anti-Ig antibodies.

B. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007): Sambrook et al., MOLECULAR CLONING, A LABORATORY MANUAL, Cold Springs Harbor Press (Cold Springs Harbor, N.Y. 1989).

Multiplex assays are analyses that simultaneously measure the levels of more than one analyte in a single sample. Multiplex assay methods and reagents are described, e.g., in U.S. Pat. No. 6,773,578 and WO2008148883.

The term "solid support" is used herein to denote a solid inert surface or body to which an agent, such as an antibody or an antigen can be immobilized. Non-limiting examples include plastic, nitrocellulose, membranes, chips, magnetic or non-magnetic beads, and particles. The term "immobilized" as used herein denotes a molecular-based coupling that is not significantly de-coupled under the conditions imposed during the steps of the assays described herein. Such immobilization can be achieved through a covalent bond, an ionic bond, an affinity-type bond, or any other chemical bond.

The term "particle" is used herein to refer to a solid or semisolid body, often with linear dimensions on the micron scale (i.e., less than 100 microns), of any shape or surface texture. Except as noted, the term is used interchangeably with "microparticle," which refers to a micron scale particle, and "bead," which refers to particles that are spherical or near-spherical in shape, often polymeric in composition.

The terms "receptacle," "vessel," "tube," "well," "compartment," etc. refer to a container that can hold reagents or an assay. If the receptacle is in a kit and holds reagents, it will typically be closed or sealed. If the receptacle is being used for an assay, it will typically be open or accessible during steps of the assay.

The terms "sample" and "biological sample" encompass a variety of sample types obtained from an organism. The term encompasses bodily fluids such as saliva, sputum, blood, blood components, serum, plasma, urine and other liquid samples of biological origin, solid tissue biopsy, tissue cultures, or supernatant taken from cultured patient cells. In the context of the present disclosure, the biological sample is typically a bodily fluid with detectable amounts of antibodies, e.g., sputum, mucus, mucosal tissue biopsy, or scrape. The biological sample can be processed prior to assay, e.g., to remove cells or cellular debris. The term encompasses samples that have been manipulated after their procurement, such as by treatment with reagents, solubilization, sedimentation, or enrichment for certain components.

The term "antibody" as used herein refers to a polypeptide encoded by an immunoglobulin gene or immunoglobulin genes, or fragments thereof, which specifically bind and recognize an analyte (antigen). The recognized immunoglobulin light chains are classified as either kappa or lambda. Immunoglobulin heavy chains are classified as gamma, mu, alpha, delta, or epsilon, which in turn define the immunoglobulin classes, IgG, IgM, IgA, IgD and IgE, respectively. In humans, there are four subclasses of IgG, denoted IgG1, IgG2, IgG3, and IgG4.

An example of a structural unit of immunoglobulin G (IgG antibody) is a tetramer. Each such tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains, respectively.

Antibodies exist as intact immunoglobulins or as well-characterized fragments produced by digestion of intact immunoglobulins with various peptidases. Thus, for example, pepsin digests an antibody near the disulfide linkages in the hinge region to produce F(ab')2, a dimer of Fab which itself is a light chain joined to VH-CH1 by a disulfide bond. The F(ab')2 dimer can be reduced under mild conditions to break the disulfide linkage in the hinge region, thereby converting the F(ab')2 dimer into two Fab' monomers. The Fab' monomer is essentially an Fab with part of the hinge region (see, Paul (Ed.), Fundamental Immunology, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or by de novo synthesis using recombinant DNA methodologies such as single chain Fv.

Antibodies are commonly referred to according their targets. While the nomenclature varies, one of skill in the art will be familiar and understand that several names can be applied to the same antibody. For example, an antibody specific for IgM can be called "anti-IgM," "IgM antibody," "anti-IgM antibody," etc.

The terms "antigen," "immunogen," "antibody target." "target analyte," and like terms are used herein to refer to a molecule, compound, or complex that is recognized by an antibody, i.e., can be specifically bound by the antibody. The term can refer to any molecule that can be specifically recognized by an antibody, e.g., a polypeptide, polynucleotide, carbohydrate, lipid, chemical moiety, or combinations thereof (e.g., phosphorylated or glycosylated polypeptides, etc.). One of skill will understand that the term does not indicate that the molecule is immunogenic in every context, but simply indicates that it can be targeted by an antibody.

Antibodies bind to an "epitope" on an antigen. The epitope is the localized site on the antigen that is recognized and bound by the antibody. Epitopes can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See. e.g., Epitope Mapping Protocols in Methods in Molecular Biology, Vol. 66, Glenn E. Morris, Ed (1996).

The terms "specific for," "specifically binds," and like terms refer to a molecule (e.g., antibody or antibody fragment) that binds to its target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, an antibody that specifically binds a given antibody target will typically bind the antibody target with at least a 2-fold greater affinity than a non-antibody target. Specificity can be determined using standard methods, e.g., solid-phase ELISA immunoassay's (see. e.g., Harlow & Lane, Using Antibodies. A Laboratory Manual (1998) for a description of immunoassay formats and conditions that can be used to determine specific immunoreactivity).

The term "binds" with respect to an antibody target (e.g., antigen, analyte), typically indicates that an antibody binds a majority of the antibody targets in a pure population (assuming appropriate molar ratios). For example, an antibody that binds a given antibody target typically binds to at least $2/3$ of the antibody targets in a solution (e.g., at least any of 75, 80, 85, 90, 91, 92, 93, 94, 95, 96, 97, 98, 99, or 100%). One of skill will recognize that some variability will arise depending on the method and/or threshold of determining binding.

The terms "label," "detectable label, "detectable moiety," and like terms refer to a composition detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA), biotin, digoxigenin, $^{32}P$ and other isotopes, haptens, and proteins which can be made detectable, e.g., by incorporating a radiolabel into the peptide or used to detect antibodies specifically reactive with the peptide. The term includes combinations of single labeling agents, e.g., a combination of fluorophores that provides a unique detectable signature, e.g., at a particular wavelength or combination of wavelengths. Any method known in the art for conjugating label to a desired agent may be employed, e.g., using methods described in Hermanson, *Bioconjugate Techniques* 1996, Academic Press, Inc., San Diego.

The term "positive," when referring to a result or signal, indicates the presence of an analyte or item that is being detected in a sample, in this case, antibody indicative of syphilis infection. The term "negative," when referring to a result or signal, indicates the absence of an analyte or item that is being detected in a sample. Positive and negative are typically determined by comparison to at least one control, e.g., a threshold level that is required for a sample to be determined positive, or a negative control (e.g., a known blank).

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters, and will understand which controls are valuable in a given situation and be able to analyze data based on comparisons to control values. Controls are also valuable for determining the significance of data. For example, if values for a given parameter are variable in controls, variation in test samples will not be considered as significant.

A "calibration control" is similar to a positive control, in that it includes a known amount of a known analyte. In the case of a multiplex assay, the calibration control can be designed to include known amounts of multiple known analytes. The amount of analyte(s) in the calibration control can be set at a minimum cut-off amount, e.g., so that a higher amount will be considered "positive" for the analyte(s), while a lower amount will be considered "negative" for the analyte(s). In some cases, multilevel calibration controls can be used, so that a range of analyte amounts can be more accurately determined. For example, an assay can include calibration controls at known low and high amounts, or known minimal, intermediate, and maximal amounts.

Controls can also be designed to ensure integrity of the sample (e.g., to detect a component in a given sample type that is known to be universally present at a certain level), or the integrity of a signal (e.g., to detect a fluorophore added in a known amount). These controls can be internal (run in the same sample that is being tested), or external (run separate from the sample that is being tested). In some embodiments, the presently disclosed assays include a control for sample quality. The sample quality control can include a solid support coated with a reagent that binds a blood component such as a clotting factor, albumin. globulin, or fibrinogen (e.g., anti-Factor XIII, see, e.g., WO2013192445). This component (e.g., a serum verification bead or SVB) ensures that serum or plasma is present and of a baseline quality. The sample quality control can also include a reagent blank bead (RBB) alone, or in combination with the solid support coated with a reagent that binds a blood component. This component serves to identify and/or quantify non-specific binding in the sample. In some embodiments, the presently disclosed assays include a signal quality control. e.g., alone or in combination with the sample quality control. The signal quality control can be a solid support with an intrinsic fluorescence, or coated with a known amount of fluorophore. This component (e.g., internal standard bead or ISB) can be useful for detecting and compensating for detector fluctuations that may occur during analysis.

The term "diagnosis" refers to a relative probability that a subject has an infection, disorder or disease. Similarly, the term "prognosis" refers to a relative probability that a certain future outcome may occur in the subject. For example, in the context of the present disclosure, prognosis can refer to the likelihood that an individual will be infected in the future (e.g., unlikely if immunized). The terms are not intended to be absolute, as will be appreciated by any one of skill in the field of medical diagnostics.

"Subject." "patient." "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc.

C. Multiplex Assays for Detecting Treponemal and Nontreponemal Antibodies

The presently described assays involve detection of more than one analyte in a single assay, and are thus described as multiplex assays. The presently described assays include components for immobilizing multiple analytes on distinguishable solid supports so that each of the multiple analytes can be identified and quantified by flow cytometry. Assay components and considerations include the solid supports and how to distinguish the different types of solid supports from one another (e.g., labels or other differentiation parameters), components to specifically immobilize the desired analytes and remove other sample materials, and labels for detecting and quantifying the desired analytes.

In this case, the multiplex assay includes a hydrophobic component, e.g., a solid support coupled to lipid antigen (e.g., cardiolipin-lecithin-cholesterol), and a hydrophilic component e.g., solid support coupled to a syphilis antigen (e.g., r15, r17, r47, or mixtures or fusions thereof). Beads are commonly functionalized for attachment to proteins (explained in more detail below), but attachment of the lipid antigen in such a manner as to allow simultaneous processing with the syphilis antigen-coated beads is carried out with specific considerations.

1. Coupling of Nontreponemal Antigens to Solid Supports

Nontreponemal Antigen Mixture (RPR or VDRL)

The nontreponemal antigen mixture can be in an ethanol solution of cardiolipin (a diphosphatidylglycerol purified from beef heart or synthetic), lecithin (from hen egg yolk, soy bean, or synthetic), and cholesterol, wherein the weight ratio of cardiolipin, lecithin and cholesterol is in the range of 0.03-1 mg/mL, 0.01-3 mg/mL, and 0.1-10 mg/mL respectively. Other organic solvents like methanol, chloroform, benzene and acetone could also be used to solubilize the nontreponemal (RPR or VDRL) antigen. The examples show use of VDRL antigen with 0.3 mg/mL cardiolipin, 2.1 mg/mL lecithin, and 9 mg/mL cholesterol.

Nontreponemal Antigen/Bead Coupling

To ensure enough positive charges on the bead surface for ionic interaction with the nontreponemal antigen mixture, the pH of the coupling buffer can be below the pI of amine functionalized beads, usually between 5 to 8. Examples include MES buffer pH 6.1, phosphate buffer pH 7.0, and MOPS buffer pH 7.4.

The positively charged ligand coupled to the bead can be an amine functional molecule, including but not limited to ethylenediamine, N,N-Diethylethylenediamine, other amine compounds, or polycationic polymers such as but not limiting polyethyleneimine (PEI). PEI can include linear or branched polyethyleneimines that contain primary, secondary or tertiary amino groups with molecular weights ranging from 1000 to 1,000,000 daltons, or polylysine and other copolymers with molecular weights ranging from 1,000 to 300,000 daltons. In some embodiments, the polylysine is between 15,000 and 30,000 daltons.

2. Coupling of Treponemal Antigens to Solid Supports

The treponemal antigen (e.g., r15, r17, and r47, or subcombinations, mixtures, or fusions thereof) can be coupled to a solid support via covalent bonding. In some embodiments, the solid support is carboxylated, to allow for convenient addition of functional groups (e.g., carboxylated beads). In some embodiments, the carboxylated support is activated and esterified before adding the treponemal antigen. Carboxyl activation can be achieved using a water soluble carbodiimide, such as 1-ethyl-3-(3-dimethylaminopropyl) carbodiimide (EDC), 1-cyclohexyl-3-(2-morpholinoethyl) carbodiimide (CMC), or dicyclohexylcarbodiimide (DCC). Esterification can be achieved, e.g., using NHS, NHSS or HOBt.

After the carboxyl activation and esterification, the treponemal antigen can added to the activated surface in buffers with pH between 6-10. Examples include MES buffer pH 6.1, phosphate buffer pH 7.0, MOPS buffer pH 7.4, and carbonate buffer pH 9.0.

After the coupling, the solid support (e.g., beads) can be blocked in buffers containing protein blockers such as BSA, casein, milk powder, mouse IgG, bovine gamma globulin (BGG), animal serum (goat, horse, murine). For example, the protein blocker(s) can be present in an amount ranging from 0.1-10 weight/volume percent.

3. Storage Buffer

Beads coated with nontreponemal antigen can be suspended in an aqueous buffer pH 5-10, e.g., 6-8. The nontreponemal antigen-coated beads can be stored with, or separate from beads coated with treponemal antigen. Various buffers such as Trizma, glycine, and phosphate can be used, with the latter being most common. The concentration of buffer will generally be in the range of approximately 0.001 to 0.1 M, e.g., 0.01-0.05 M. The buffer can contain a salt such as sodium chloride, e.g., in the range of approximately 0.01 to 0.5 M or 0.05-0.2 M. In some embodiments, the storage buffer further comprises cholesterol.

Non-ionic detergents such as Tween-20 can exert a deleterious effect on the hydrophobic micro environment on the nontreponemal antigen (e.g., RPR) coated beads. This can lead to nontreponemal antigen instability and poor assay performance (e.g., reduced affinity of RPR-specific antibodies for antigen).

Accordingly, for storage or running the assay, non-ionic detergent can be omitted and replaced with additives that minimize or mitigate instability, and that stabilize the individual antigen(s) or improve the assay performance. Particularly, ethylenediaminetetraacetic acid (EDTA) can be employed in amounts of approximately 0.1 to 1.0 weight/volume (w/v) percent. CHAPS or other zwitterionic detergents such as CHAPSO, IGEPAL and Zwittergent 3-8, 3-10, 3-12, 3-14 and 3-16 can be employed, for example, in amounts of approximately 0.01 to 0.5 w/v percent. BSA can be employed, for example, in amounts of approximately 0.01 to 3 w/v percent. Glycerol can be employed, for example, in amounts of approximately 0.05 to 25 w/v percent. Sodium azide can be employed in amounts of approximately 0.005 to 0.1 w/v percent.

The conjugate reagent buffer optionally also include cholesterol in concentrations of 30-150 µg/mL, 30-100 µg/mL, 30 µg/mL, 35 µg/mL, 40 µg/mL or 50 µg/mL. In some embodiments, the cholesterol is bovine cholesterol.

4. Assay Buffers

Assay buffers (e.g., for carrying out antibody-binding assays with the combined beads) can include a buffer such as phosphate, MOPS, triethanolamine (TEA), HEPES, TES, EPPS or Trizma. In some embodiments, the buffer is in a concentration of 10-100 mM, for example, at pH 6.0 to 8.0. The buffer can further comprise sodium chloride, e.g., at 50-300 mM. In some embodiments, the buffer contains protein stabilizers such as BSA, casein, milk powder, mouse IgG, bovine gamma globulin (BGG), animal serum (goat, horse, murine). In some embodiments, the protein stabilizer(s) is in an amount ranging from 0-10% of the final volume. Buffers may contain preservatives including but not limited to ProClin 300, ProClin 900, sodium benzoate and sodium azide.

All buffers can contain ionic and zwitterionic detergents such as CHAPS, IGEPAL, CHAPSO and Zwittergent 3-8, 3-10, 3-12, 3-14 and 3-16, e.g., in concentrations between 0.05 to 1.0 or 0.1-0.5 volume percent.

5. Wash Buffers

Wash buffers (e.g., for removing non-reactive reagent and non-specific bindings on beads after each incubation step) can include a buffer such as phosphate, MOPS, triethanolamine (TEA), HEPES, TES, EPPS or Trizma. The buffer can be at a concentration of, e.g., 10-100 mM, e.g., at pH 6.0 to 8.0. The buffer can further comprise sodium chloride, e.g., at 50-300 mM. In some embodiments, the wash buffer may contain Tween-20 or non-ionic detergent such as Tween 40, Tween 60, and Triton X-100, in concentrations between 0.05 to 1.0 or 0.1-0.5 volume percent.

6. Controls

Controls (e.g., internal controls) can be used with the presently described assays. An internal standard (e.g., internal standard bead or ISB) can be used to rectify fluctuations in signals due to voltage spikes or progressive changes in detector temperature or other factors that affect detector performance. The internal standard has inherent fluorescence that is independent of assay chemistry. For example, the internal standard can be derivatized with tetramethylrhodamine, or other stable label that does not interfere with or overlap with labels being used to detect sample components.

A sample control can also be used to ensure that sample, e.g., serum or plasma, has been introduced in the reaction and has not been diluted. A sample control can include a solid support coated with an agent that binds to a component of the sample, for example, a serum verification bead (SVB). The serum verification support can be coated with anti-Factor XIII antibody. Soluble Factor XIII (ß subunit) can be measured in a sandwich-type immunoassay. A sample control can also include a reagent blank control, e.g., a solid support that is not coated with anything, to detect background binding of sample to the solid support.

7. Solid Supports

As explained above, the presently described multiplex assays involve use of a solid support, typically particles (also referred to as microparticles or beads). For detection by flow cytometry, particles that emit autofluorescence should be avoided since this will increase background signal and render them unsuitable. Particles created by standard emulsion polymerization from a variety of starting monomers generally exhibit low autofluorescence, while those that have been modified to increase porosity ("macroporous" particles) exhibit high autofluorescence. Autofluorescence in such particles further increases with increasing size and increasing percentage of divinylbenzene monomer.

The size range of the microparticles can vary and particular size ranges are not critical. In most cases, the aggregated size range of the microparticles lies within the range of from about 0.3 micrometers to about 100 micrometers in particle diameter, e.g., within the range of from about 0.5 micrometers to about 40 micrometers.

Magnetic particles are commonly used in the art, and can make separation and wash steps more convenient for the presently described assays. "Magnetic particles," "magnetically responsive material," "magnetic beads," and like terms denote a material that responds to a magnetic field. Magnetically responsive materials include paramagnetic materials (e.g., iron, nickel, and cobalt, as well as metal oxides such as $Fe_3O_4$, $BaFe_{12}O_{19}$, CoO, NiO, $Mn_2O_3$, $Cr_2O_3$, and CoMnP), ferromagnetic materials, ferrimagnetic materials, and metamagnetic materials. Rather than constituting the entire microparticle, the magnetically responsive material typically constitutes one component of the microparticle, while the remainder consists of a polymeric material which can be chemically derivatized to permit attachment of an assay reagent (e.g., antigen or antibody). Attachment of the assay reagent can be either direct (e.g., covalent) or indirect (e.g., through ionic or other affinity interactions).

Methods of, and instrumentation for, applying and removing a magnetic field as part of an assay are known to those skilled in the art and reported in the literature. Examples of literature reports are Forrest et al., U.S. Pat. No. 4,141,687: Ithakissios, U.S. Pat. No. 4,115,534; Vlieger et al., *Analytical Biochemistry* 205:1-7 (1992): Dudley, *Journal of Clinical Immunoassay* 14:77-82 (1991); and Smart, *Journal of Clinical Immunoassay* 15:246-251 (1992).

The polymeric matrix that forms the microparticle can be any material that is compatible with the presently described assays. The matrix should be inert to the components of the biological sample and to the assay reagents, have minimal autofluorescence, be solid and insoluble in the sample and in any other reagents or washes used in the assay, and capable of affixing an assay reagent to the microparticle. Examples of suitable polymers are polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle.

Functional groups for attachment of an assay reagent (e.g., antigen or antibody) can be incorporated into the polymer structure by conventional means. Examples of suitable functional groups are amine groups, ammonium groups, hydroxyl groups, carboxylic acid groups, and isocyanate groups. Assay reagent is typically covalently bound to the solid phase surface, either directly or indirectly, e.g., with a linking group. Linking groups can be used as a means of increasing the density of reactive groups on the solid phase surface and decreasing steric hindrance to increase the range and sensitivity of the assay, or as a means of adding specific types of reactive groups to the solid phase surface to broaden the range of types of assay reagents that can be affixed to the solid phase. Examples of suitable useful linking groups are polylysine, polyaspartic acid, polyglutamic acid and polyarginine.

Microparticles of different types in a multiplex assay can be distinguished from one another, e.g., by size, weight, light scatter or absorbance, reflectance, shape, or label, e.g., fluorescent label.

Where microparticle size is used as a differentiation factor (distinguishing characteristic), the widths of the size subranges and the spacing between mean diameters of adjacent subranges are selected to permit differentiation of different types of microparticles by flow cytometry, as will be apparent to those skilled in the use of and instrumentation for flow cytometry. Typically, a subrange for a given mean diameter is about ±5% CV or less of the mean diameter, where CV is the coefficient of variation and is defined as the standard deviation of the particle diameter divided by the mean particle diameter times 100 percent. The mean diameters of subranges for different types of particles are generally spaced apart by at least about 6% of the mean diameter of one of the subranges, e.g., at least about 8% or 10% of the mean diameter of one of the subranges.

Light scatter can also be used to distinguish different types of microparticles. Side angle light scatter varies with particle size, granularity, absorbance and surface roughness, while forward angle light scatter is mainly affected by size and refractive index. Varying any of these qualities can result in light scatter differences that can serve as a means of distinguishing the various groups.

Still another example of a differentiation parameter is absorbance. When light is applied to particles, the absorbance of the light by the particles is indicated mostly by a change in the strength of the laterally (side-angle) scattered light while the strength of the forward-scattered light is relatively unaffected. Consequently, the difference in absorbance between various colored dyes associated with the particles is determined by observing differences in the strength of the laterally scattered light.

A wide array of parameters or characteristics can be used as differentiation parameters to distinguish the particles of one group from those of another. The differentiation parameters may arise from particle size, composition, physical characteristics that affect light scattering, excitable fluorescent dyes or colored dyes that impart different emission spectra and/or scattering characteristics to the particles, or from different concentrations of one or more fluorescent dyes.

When the distinguishable characteristic is a fluorescent dye or color, it can be coated on the surface of the microparticle, embedded in the microparticle, or bound to the molecules of the microparticle material. Thus, fluorescent microparticles can be manufactured by combining the polymer material with the fluorescent dye, or by impregnating the microparticle with the dye. Microparticles with dyes already incorporated and thereby suitable for use in the present invention are commercially available, from suppliers such as Spherotech, Inc. (Libertyville, Ill., USA) and Molecular Probes, Inc. (Eugene, Oreg., USA). A list of vendors of flow cytometric products can be found, e.g., at the website of molbio.princeton.edu/facs/FCMsites.html.

8 Detectable Labels

The presently described assays can have several labeled components, e.g., beads, secondary antibodies (e.g., labeled, anti-Ig antibodies), signal quality and sample quality controls. Labels can be any substance or component that directly or indirectly emits or generates a detectable signal. In some embodiments, the labels are fluorophores, many of which are reported in the literature and thus known to those skilled in the art, and many of which are readily commercially available. Literature sources for fluorophores include Cardullo et al., *Proc. Natl. Acad. Sci. USA* 85: 8790-8794 (1988); Dexter, *J. of Chemical Physics* 21: 836-850 (1953); Hochstrasser et al., *Biophysical Chemistry* 45: 133-141 (1992); Selvin, *Methods in Enzymology* 246: 300-334 (1995); Steinberg, *Ann. Rev. Biochem.*, 40: 83-114 (1971): Stryer, *Ann. Rev. Biochem.* 47: 819-846 (1978): Wang et al., *Tetrahedron Letters* 31: 6493-6496 (1990); and Wang et al., *Anal. Chem.* 67: 1197-1203 (1995).

The following are examples of fluorophores that can be used as labels:
4-acetamido-4'-isothiocyanatostilbene-2,2'disulfonic acid
acridine
acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin
7-amino-4-methylcoumarin (AMC, Coumarin 120)
7-amino-4-trifluoromethylcoumarin (Coumaran 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin
eosin isothiocyanate
erythrosin B
erythrosin isothiocyanate
ethidium
5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)
fluorescein
fluorescein isothiocyanate
fluorescamine
IR144
IR1446
Malachite Green isothiocyanate
4-methylumbelliferone
ortho cresolphthalein
nitrotyrosine
pararosaniline
Phenol Red
phycoerythrin (including but not limited to B and R types)
o-phthaldialdehyde
pyrene
pyrene butyrate
succinimidyl 1-pyrene butyrate
quantum dots
Reactive Red 4 (Cibacron™ Brilliant Red 3B-A)
6-carboxy-X-rhodamine (ROX)
6-carboxyrhodamine (R6G)
lissamine rhodamine B sulfonyl chloride rhodamine
rhodamine B
rhodamine 123
rhodamine X isothiocyanate
sulforhodamine B
sulforhodamine 101
sulfonyl chloride derivative of sulforhodamine 101 (Texas Red)
N,N,N',N'-tetramethyl-6-carboxyrhodamine (TAMRA)
tetramethyl rhodamine
tetramethyl rhodamine isothiocyanate (TRITC)
riboflavin
rosolic acid
lanthanide chelate derivatives A prominent group of fluorophores for immunoassays are fluorescein, fluorescein isothiocyanate, phycoerythrin, rhodamine B, and Texas Red (sulfonyl chloride derivative of sulforhodamine 101). Any of the fluorophores in the list preceding this paragraph can be used in the presently described assays, either to label the microparticle, or to label a binding agent (e.g., an antibody or streptavidin). Fluorochromes can be attached by conventional covalent bonding, using appropriate functional groups on the fluorophores and on the microparticle or binding agent. The recognition of such groups and the reactions to form the linkages will be readily apparent to those skilled in the art. Other labels that can be used in place of the fluorophores are radioactive labels and enzyme labels. These are likewise known in the art.

D. Detection of Treponemal and Nontreponemal Antibodies

Once solid supports are coated with treponemal and nontreponemal antigens as described above, the coated solid supports are contacted with sample, e.g., biological sample from an individual suspected of having been exposed to syphilis, e.g., in the presence of assay buffer as described above. Unbound sample can be washed away. In this assay, 3, 4 or 5 wash steps can be used. Labeled anti-Ig antibodies are added to allow for detection of antibodies from the sample bound to the solid supports. Where the sample is from a human, labeled anti-human Ig antibodies are used. For example, a mixture of anti-IgG and anti-IgM antibodies, or an antibody that binds both IgG and IgM, can be used.

Flow cytometry can be used to detect size, weight, light scatter, and fluorescence of assay components. Flow cytometry methods and instrumentation are known in the art. Descriptions of instrumentation and methods can be found, e.g., in Introduction to Flow Cytometry: A Learning Guide (2000) Becton, Dickinson, and Company; McHugh, "Flow Microsphere Immunoassay for the Quantitative and Simultaneous Detection of Multiple Soluble Analytes," Methods in Cell Biology 42, Part B (Academic Press, 1994).

Flow cytometry in general involves passage of a suspension (e.g., beads or microparticles) as a stream past a light beam and electro-optical sensors, in such a manner that only one particle at a time passes through the region. As each particle passes this region, the light beam is perturbed by the presence of the particle, and the resulting scattered and fluorescent light is detected. The optical signals are used by the instrumentation to identify the subgroup to which each particle belongs, along with the presence and amount of label, so that individual assay results are achieved. Descriptions of instrumentation and methods for flow cytometry are found in the literature. Examples are McHugh, "Flow Microsphere Immunoassay for the Quantitative and Simultaneous Detection of Multiple Soluble Analytes," *Methods in Cell Biology* 42, Part B (Academic Press, 1994); McHugh et al., "Microsphere-Based Fluorescence Immunoassays Using Flow Cytometry Instrumentation," *Clinical Flow Cytometry*, Bauer, K. D., et al., eds. (Baltimore, Maryland, USA: Williams and Williams, 1993), pp. 535-544; Lindmo et al., "Immunometric Assay Using Mixtures of Two Particle Types of Different Affinity," *J. Immunol. Meth.* 126: 183-189 (1990); McHugh, "Flow Cytometry and the Application of Microsphere-Based Fluorescence Immunoassays," *Immunochemica* 5: 116 (1991); Horan et al., "Fluid Phase Particle Fluorescence Analysis: Rheumatoid Factor Specificity Evaluated by Laser Flow Cytophotometry," *Immunoassays in the Clinical Laboratory*, 185-189 (Liss 1979); Wilson et al., "A New Microsphere-Based Immunofluorescence Assay Using Flow Cytometry," *J. Immunol. Meth.* 107: 225-230 (1988).

Signal can also be detected by a fluorescent imager (e.g., a Luminex Magpix®), e.g., for assays run in an ELISA format (e.g., on a microtiter plate). In addition, for beads or plates, signal detection can be carried out using an addressable array (e.g., an Illumina detector or similar system).

E. Kits

Also provided are kits for detecting treponemal and nontreponemal antibodies as described herein. In some embodiments, the kit comprises (i) solid supports (e.g., beads) coupled to nontreponemal antigen and (ii) solid supports (e.g., beads) coupled to treponemal antigen. In some embodiments, the solid supports of (i) and (ii) are in the same storage compartment (e.g., tube or vial). In some embodiments, the solid supports of (i) and (ii) are in the separate storage compartments. In some embodiments, the solid supports of (i) are PEI-functionalized.

The kit can also comprise other reagents, e.g., secondary antibodies, assay buffers, wash buffers, and stock solutions (e.g., concentrated buffers). In some embodiments, the secondary antibody is labeled anti-human Ig as described herein. In some embodiments, the kit can include consumables such as multiwell plates or tubes for carrying out the assay.

F. Examples

1. Example 1

This example illustrates the performance of the combination treponemal and nontreponemal test (detecting antibodies against syphilis antigen and lipoidal antigen, respectively) against comparators on a set of 113 clinical serum samples with known disease stages and treatment status, and 285 syphilis test ordered samples. Patient samples were tested for the presence of treponemal and nontreponemal antibodies using the BioPlex™ 2200 platform as shown in FIG. 1.

As shown in FIG. 1, beads coated with a recombinant treponemal r17-r47 fusion protein (Rec Tp17/r47 fusion) and PEI-functionalized beads coated with non-treponemal antigens cardiolipin, lecithin, and cholesterol were mixed in assay buffer (50 mM MOPS, 150 mM NaCl, 0.05% BSA, 10 mM EDTA, 0.1% CHAPS, 20% glycerol, and 0.095% sodium azide). The two sets of analyte beads are distinguishable via different labels (R17 vs. R21 for treponemal vs. nontreponemal beads). Two sets of control beads were used, a serum verification bead coated with FXIII and an internal standard bead derivatized with tetramethylrhodamine. These are distinguishable due to a unique combination of fluorescent dyes (classification dyes). Samples were diluted with a sample dilution buffer (50 mM TEA, 150 mM NaCl, 75 mM $MgCl_2$, 3% BSA, 0.03% mouse IgG, 0.47% gamma globulin, 0.0015% PSMA, 10 IU/L aprotinin, 0.1% sodium benzoate, 0.095% sodium azide, 0.3% ProClin, at pH 7.4). Diluted sample was added, each sample potentially including anti-treponemal antibodies (IgG anti-Syph Ab and IgM anti-Syph Ab) and anti-nontreponemal antibodies (IgG anti-CrL Ab and IgM anti-CrL Ab). After 20 minutes incubation, the beads were washed in wash buffer containing 50 mM PBS and 0.1% Tween-20. The beads where then incubated with a conjugate reagent (labeled secondary antibody specific for human IgG and IgM). The conjugate reagent in this case was a bispecific anti-human IgG and anti-human IgM labeled with PE in a solution of 50 mM sodium phosphate, 150 mM NaCl, 1% BSA, 0.1% mouse IgG, 3.3 IU/L aprotinin, 0.1% sodium benzoate, 0.095% sodium azide, and 0.3% ProClin at pH 7.4. After 10 minutes incubation, the beads were washed a second time in wash buffer including 50 mM PBS and 0.1% Tween-20.

Subsequently, washed beads were suspended in sheath fluid (phosphate buffer saline (PBS) containing 0.3% ProClin 300 and 0.095% sodium azide) and sent to the detector. The fluorescent dye signature and the presence of bound antibodies were detected for each bead by flow cytometer. Treponemal and/or nontreponemal specific signal associated with each bead was compared to matched controls and results reported. Dividing the test bead signal by the ISB signal (fluorescent ratio) can rectify signal within and between runs including controls for detector stability and fluctuations.

A comparison of results obtained from combo test and those from comparators are listed in Tables 1 and 2.

against the treponemal and lipoidal antigen was evaluated using 228 RPR/VDRL positive serum samples, 226 Syphilis test ordered serum samples and 122 clinical serum samples with known disease stages and treatment status. Subsequently, the results from the combination test were compared head-to-head with the Diasorin Liaison™ treponema

TABLE 1

| Syphilis category | Treatment Status | Numer of Samples | BioPlex syphilis combo test | | | | Comparator test | | | |
| --- | --- | --- | --- | --- | --- | --- | --- | --- | --- | --- |
| | | | Treponemal assay | | Non-treponemal assay | | Treponemal assay | | Non-treponemal assay | |
| | | | R* | NR** | R | NR | R | NR | R | NR |
| Primary | Untreated | 8 | 8 | 0 | 7 | 1 | 8 | 0 | 7 | 1 |
| | Treated | 24 | 21 | 3 | 20 | 4 | 21 | 3 | 17 | 7 |
| Secondary | Untreated | 17 | 17 | 0 | 14 | 3 | 17 | 0 | 17 | 0 |
| | Treated | 25 | 25 | 0 | 16 | 9 | 25 | 0 | 15 | 10 |
| Latent | Untreated | 7 | 7 | 0 | 5 | 2 | 7 | 0 | 6 | 1 |
| | Treated | 32 | 31 | 1 | 21 | 11 | 31 | 1 | 21 | 11 |
| Total Medically diagnosed syphilis samples | | 113 | 109 | 4 | 83 | 30 | 109 | 4 | 83 | 30 |
| Syphilis negative samples | | 285 | 1 | 284 | 3 | 282 | 1 | 284 | 0 | 285 |

Note:
*R is reactive,
**NR is non-reactive.

TABLE 2

| | | BioPlex syphilis combo test | | | |
| --- | --- | --- | --- | --- | --- |
| | | Treponemal assay | | Non-treponemal assay | |
| Syphilis category | Numer of Samples | % Positive Agreement | % Negative Agreement | % Positive Agreement | % Negative Agreement |
| Medically diagnosed syphilis samples | 113 | 100% (109/109) | N/A | 92.7% (77/83) | N/A |
| Syphilis test ordered samples | 285 | N/A | 99.6% (283/284) | N/A | 98.9% (282/285) |

For medically diagnosed syphilis samples, excellent agreement was observed between the clinically diagnosed untreated and treated primary secondary and latent infections and the combination treponemal test as well as the comparator test. The combination test detected non-treponemal antibody in 20 of 24 treated primary disease specimens, 14 of 17 treated secondary disease specimens, 16 of 25 untreated secondary disease specimens, and 5 of 7 untreated latent disease samples: while the comparator non-treponemal test detected in 17 of 24 treated primary disease, 17 of 17 treated secondary disease, 15 of 25 untreated secondary disease, and 6 of 7 untreated latent disease specimens. Of the 285 Syphilis negative samples, 284 tested negative for treponemal antibodies and 282 for non-treponemal antibodies. Overall, the combination test exhibits 100% sensitivity and 99.6% specificity for treponemal antibody assay, and 92.7% sensitivity and 98.9% specificity for non-treponemal antibody assays respectively.

2. Example 2

In a second example the performance of the combination treponemal and non-treponemal test detecting antibodies (both IgG and IgM for both treponemal and non-treponemal)

assay or Fujirebio Serodia™ TPPA assay and BD Macro-Vue™ RPR card test (Tables 3-5).

For the RPR/VDRL positive sample cohort, a positive agreement of 99.5% (211/212) and a negative agreement of 100% (14/14) was observed between the treponemal component of the combination test and the Liaison™ Treponema assay, Table 3a. In contrast, a comparison between the non-treponemal component of the combination test and BD Macro-Vue RPR card test revealed a positive agreement of 99.1% (217/219) and a negative agreement of 71.4% (5/7), Table 3b.

Table 3. Head-to-Head Comparison Between the Combination Assay Treponemal Component and Liaison™ Treponema Assays (3a) and Between the Combination Non-Treponemal Assay Component and BD Macro-Vue™ RPR Assays (3b) Using 226 RPR/VDRL Positive Sample Cohort.

TABLE 3a

| | | Liaison ™ Treponema | | | |
| --- | --- | --- | --- | --- | --- |
| | | Positive | Negative | Equivocal | Total |
| Combination Assay Treponemal | Positive | 211 | 0 | 0 | 211 |
| | Negative | 1 | 14 | 0 | 15 |
| | Equivocal | 0 | 0 | 0 | 0 |
| | Total | 212 | 14 | 0 | 226 |

TABLE 3b

| | | BD Macro-Vue ™ RPR | | |
| --- | --- | --- | --- | --- |
| | | Positive | Negative | Total |
| Combination Assay Non-treponemal | Positive | 217 | 2 | 219 |
| | Negative | 2 | 5 | 7 |
| | Total | 219 | 7 | 226 |

Under similar assay conditions the test ordered sample cohort displayed a positive agreement of 93.3% (28/32) and a negative agreement of 97.5% (193/198) between the treponemal component of the combination assay and the Liaison™ Treponema assay, Table 4a. Within the same population the positive and negative agreement between the non-treponemal component of the combination assay and manual BD Macro-Vue RPR card test was 95% (19/20) and 99.5% (207/208) respectively, Table 4b.

Table 4. Head-to-Head Comparison Between the Combination Assay Treponemal Component and Liaison™ Treponema Assay (2a) and Between the Combination Non-Treponemal Assay Component and BD Macro-Vue RPR Assays (2b) Using 228 Test Ordered Sample Cohort.

TABLE 4a

|  |  | Liaison ™ Treponema | | | |
|---|---|---|---|---|---|
|  |  | Positive | Negative | Equivocal | Total |
| Combination Assay Treponemal | Positive | 28 | 4 | 0 | 32 |
|  | Negative | 0 | 193 | 1 | 194 |
|  | Equivocal | 1 | 1 | 0 | 2 |
|  | Total | 29 | 198 | 1 | 228 |

TABLE 4b

|  |  | BD Macro-Vue ™ RPR | | |
|---|---|---|---|---|
|  |  | Positive | Negative | Total |
| Combination Assay Non-treponemal | Positive | 19 | 1 | 20 |
|  | Negative | 1 | 207 | 208 |
|  | Total | 219 | 7 | 226 |

In order to assess the clinical sensitivity of the combination assay, a total of 122 samples with known clinical status were tested, Table 5. Samples were from treated and untreated patients with primary, secondary and latent infection. While untreated samples exhibit an overall sensitivity of 97.6% (40/41), treated samples revealed a sensitivity of 95.1% (77/81) using the combination treponemal assay. When the same sample cohort was tested in parallel with the Fujirebio Serodia™ TPPA assay, an exactly equivalent sensitivity was observed for untreated and treated groups. On the other hand, the combination non-treponemal assay revealed an overall sensitivity of 95.1% (39/41) for the untreated group compared to 86.4% (70/81) for the treated group. These results are in contrast to the BD Macro-Vue™ card test that demonstrated an overall sensitivity of 95.1% for the untreated group and 75.3% for the treated group. Collectively, these results suggest higher sensitivity of the combination non-treponemal assay.

TABLE 5

Comparison of the combination assay with the Fujirebio Serodia ™ TPPA and BD Macro-Vue ™ RPR card assays using 122 clinically characterized primary, secondary and latent syphilis samples.

|  | Treponemal | | Non-treponemal | |
|---|---|---|---|---|
| Group | Combination Assay Treponemal | Serodia ™ TPPA | Combination Assay Non-treponemal | BD Micro-Vue ™ RPR |
| Untreated | 97.6% (40/41) | 97.6% (40/41) | 95.1% (39/41) | 95.1% (39/41) |
| Treated | 95.1% (77/81) | 95.1% (77/81) | 86.4% (70/81) | 75.3% (61/81) |

Figure 2:
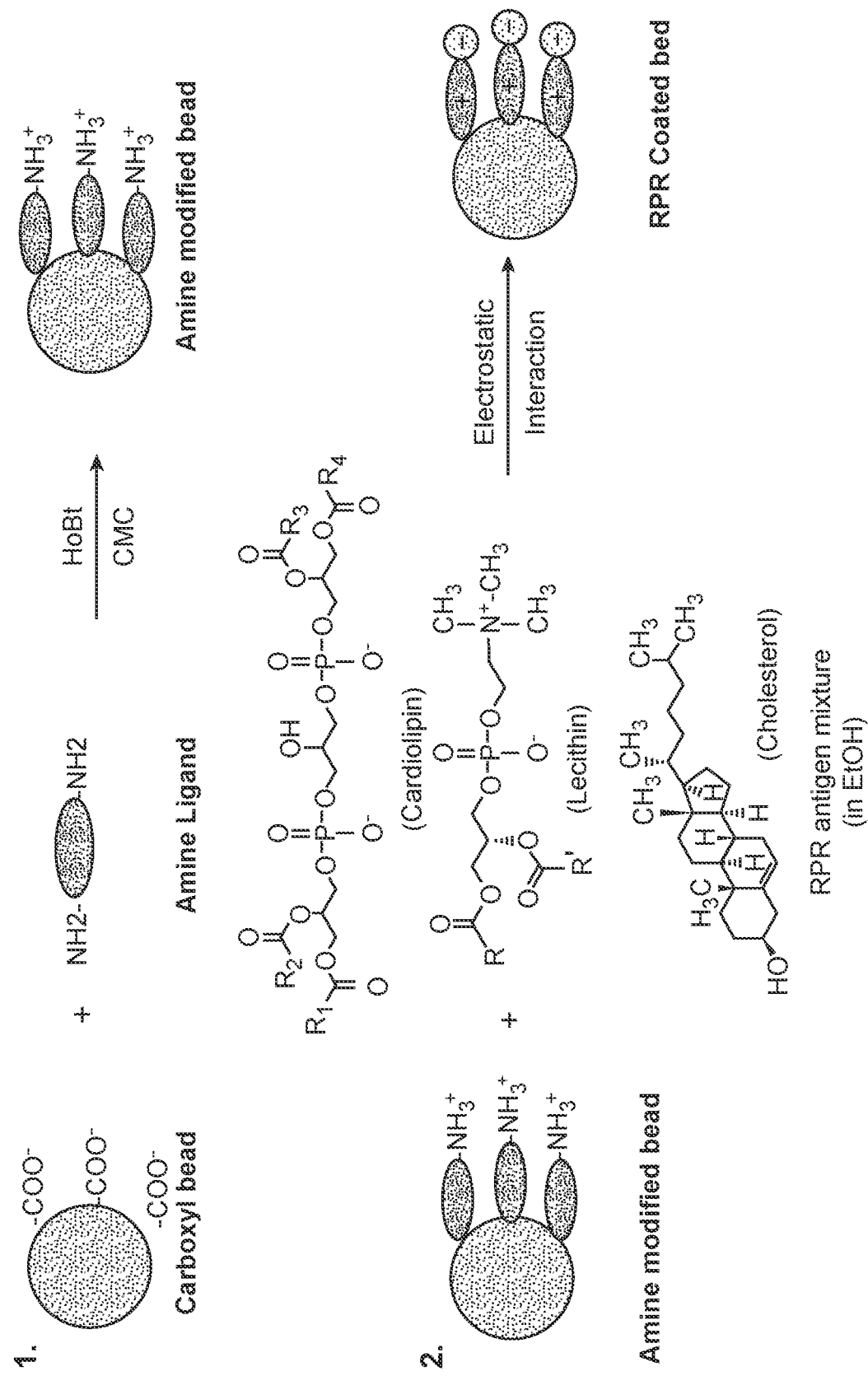
FIG. 2 depicts bead surface functionalization to allow the beads to be coated with lipid nontreponemal antigen.

3. Example 3: Functionalization of Bead Surface for Coating with Nontreponemal Antigen FIG. 2 shows an example of functionalizing a bead with amine ligand to allow for ionic interaction with lipid RPR antigen mixture. Positively charged ligand is first bound to the carboxyl beads via either passive adsorption or covalent binding to introduce positive charges on the bead surface.

Lipids (with net negative charge due to the presence of phosphate group) could not be coupled directly on activated carboxylated beads. In order to bind cardiolipin, cholesterol, and lecithin (a trio of lipids) we changed the net charge on magnetic beads by covalently coupling a positively charged group such as polyethylenimine (PEI). Beads with the cationic imino group were then incubated with negatively charged lipids. The interaction produces a stable antigen coating the bead surface as evaluated by stability studies.

As explained above, the positively charged ligand can be an amine functional molecule. We tested the ability of nontreponemal antigen (RPR) to bind to beads coated with ethylenediamine, polyethyleneimine (PEI), and poly-lysine.

TABLE 6

Performance of beads functionalized with indicated component

| Sample ID | Ethylenediamine | Poly (ethyleneimine) | Poly-Lysine | RPR |
|---|---|---|---|---|
| SS0297856 | 175 | 514 | 546 | RPR |
| SS0297418 | 289 | 866 | 902 | positive |
| JV0144150 | 161 | 228 | 254 | (Titer 64) |
| JK0490505 | 116 | 576 | 470 |  |
| JK0489744 | 114 | 502 | 498 |  |
| HB70942 | 72 | 62 | 101 | Negative |
| HB70946 | 94 | 62 | 110 |  |
| HB70953 | 53 | 49 | 67 |  |
| HB70958 | 51 | 57 | 75 |  |
| HB70964 | 55 | 57 | 92 |  |

Beads were functionalized with ethylenediamine, poly(ethyleneimine), or poly-lysine and coated with RPR. The coated beads were then exposed to RPR antibody positive samples (top 5 rows) or antibody negative samples (bottom 5 rows). In this assay, poly(ethyleneimine) (PEI) functionalized beads generally performed the best, with higher reading for positive samples and low background readings for negative samples.

The above examples are provided to illustrate the invention but not to limit its scope. Other variants of the invention will be readily apparent to one of ordinary skill in the art and are encompassed by the appended claims. All publications, databases, internet sources, patents, patent applications, and accession numbers cited herein are hereby incorporated by reference in their entireties for all purposes.

What is claimed is:

1. A kit comprising:
   (i) a cardiolipin-lecithin-cholesterol antigen non-covalently attached to a solid support, wherein the cardiolipin-lecithin-cholesterol antigen is unmodified to reduce hydrophobicity; and
   (ii) a *Treponema pallidum* antigen attached to the solid support,
   and wherein the solid support is contained in a storage buffer that lacks ionic detergent.

2. The kit of claim 1, wherein the storage buffer comprises a Zwitterionic detergent.

3. The kit of claim 2, wherein the zwitterionic detergent is CHAPS, CHAPSO, or Zwittergent 3-8, 3-10, 3-12, 3-14, or 3-16.

4. The kit of claim 1, wherein the solid support of (i) is functionalized with polyethylenimine to coat the solid support with cardiolipin-lecithin-cholesterol antigen.

5. The kit of claim 1, wherein the *Treponema pallidum* antigen is a fusion of r17 and r47.

6. The kit of claim 1, wherein the *Treponema pallidum* antigen is attached to the solid support of (ii) via a covalent interaction.

7. The kit of claim 1 further comprising a labeled, anti-human immunoglobulin (Ig) antibody.

8. The kit of claim 7, wherein the labeled, anti-human Ig antibody is specific for IgG or IgM.

9. The kit of claim 7, wherein the kit comprises a first labeled, anti-human Ig antibody specific for IgG and a second labeled, anti-human Ig antibody specific for IgM.

10. The kit of claim 9, wherein the first and second labeled, anti-human Ig antibodies have different labels.

11. The kit of claim 1, further comprising a wash or wash stock solution that comprises phosphate buffer saline.

12. The kit of claim 1, wherein the kit further comprises (iii) a solid support coated with antibodies specific for clotting factor XIII (anti-FXIII).

13. The kit of claim 1, further comprising one or more of an assay buffer, a sample dilution buffer, or a wash buffer.

14. The kit of claim 1, further comprising an assay buffer, a sample dilution buffer, and a wash buffer.

* * * * *